United States Patent
Farner et al.

(12) 
(10) Patent No.: US 6,388,120 B1
(45) Date of Patent: May 14, 2002

(54) CONTINUOUS PROCESS FOR THE MANUFACTURE OF PHOSPHORIC ACID ESTERS

(75) Inventors: Robert M. Farner; David W. Bartley, both of West Lafayette; Jon D. Lehmkuhler, Lebanon, all of IN (US)

(73) Assignee: PABU Services, Inc., Wilmington, DE (US)

( * ) Notice: Subject to any disclaimer, the term of this patent is extended or adjusted under 35 U.S.C. 154(b) by 0 days.

(21) Appl. No.: 09/301,532

(22) Filed: Apr. 28, 1999

Related U.S. Application Data

(63) Continuation-in-part of application No. 09/023,634, filed on Feb. 13, 1998, now Pat. No. 6,031,035.
(60) Provisional application No. 60/083,414, filed on Apr. 29, 1998.

(51) Int. Cl.[7] .................................................. C07F 9/09
(52) U.S. Cl. ........................ 558/92; 524/127; 558/162; 558/163
(58) Field of Search ................................. 558/122, 162, 558/163, 92; 528/287, 400; 524/127; 422/131, 164

(56) References Cited

U.S. PATENT DOCUMENTS

| | | |
|---|---|---|
| 2,520,090 A | 8/1950 | Barrett |
| 2,782,128 A | 2/1957 | Paist et al. .................... 106/177 |
| 3,174,931 A | 3/1965 | Matson et al. .............. 252/37.2 |
| 3,317,636 A | 5/1967 | Lovell et al. ................ 260/929 |
| 3,360,591 A | 12/1967 | Giammaria et al. ........ 260/930 |
| 4,134,876 A | 1/1979 | Horner et al. |
| 4,267,127 A | 5/1981 | Selbeck et al. |
| 4,343,732 A | 8/1982 | Zama et al. |
| 4,933,386 A | 6/1990 | Nitoh et al. |
| 5,011,736 A | 4/1991 | Abolins et al. |
| 5,104,450 A | 4/1992 | Sand et al. |
| 5,135,973 A | 8/1992 | Fukasawa et al. |
| 5,204,394 A | 4/1993 | Gosens et al. |
| 5,281,741 A | 1/1994 | Gunkel et al. |
| 5,294,654 A | 3/1994 | Hellstern-Burnell |
| 5,420,327 A | 5/1995 | Bright et al. |
| 5,455,292 A | 10/1995 | Kakegawa et al. ......... 524/141 |
| 5,880,308 A | * 3/1999 | Kawata et al. .............. 558/162 |
| 6,031,035 A | * 2/2000 | Bartley et al. .............. 524/126 |
| 6,083,428 A | * 7/2000 | Ueda et al. .................. 524/127 |

FOREIGN PATENT DOCUMENTS

| | | |
|---|---|---|
| EP | 0 129 824 A1 | 1/1985 |
| EP | 0 129 825 A3 | 1/1985 |
| EP | 0 509 506 A2 | 10/1992 |
| EP | 0 657 498 A1 | 6/1995 |
| EP | 0 672 717 A1 | 9/1995 |
| EP | 0 690 063 A1 | 1/1996 |
| GB | 2 043 083 A | 10/1980 |
| WO | 90/03417 | 4/1990 |
| WO | 96/06885 | 3/1996 |
| WO | 96/20263 | 4/1996 |
| WO | 96/13508 | 5/1996 |
| WO | 96/17887 | 6/1996 |

OTHER PUBLICATIONS

Abstract: Japan JP 09192506 Matsubara et al.
Abstract: Japan JP 09012587 A2 Matsubara et al.

* cited by examiner

*Primary Examiner*—Veronica P. Hoke
(74) *Attorney, Agent, or Firm*—Woodard, Emhardt, Naughton & McNett

(57) ABSTRACT

A method of making phosphoric acid esters by continuously reacting a phosphorus oxyhalide with a polyol to produce at least about 60% normalized monomeric halophosphate intermediate, and then reacting the monomeric halophosphate intermediate with an alcohol to produce a desired phosphoric acid ester is provided. In other embodiments, the reaction of the monomeric halophosphate intermediate with the alcohol can also be carried out continuously. Another aspect of the invention provides a method of making phosphoric acid esters by continuously reacting a phosphorus oxyhalide with a monohydric alcohol to produce at least about 60% normalized monohalomonophosphate diester intermediate, and then reacting the monohalomonophosphate diester intermediate with a polyol to produce a phosphoric acid ester. In other embodiments, the reaction of the monohalomonophosphate diester intermediate with the polyol may also be carried out continuously.

15 Claims, 3 Drawing Sheets

US 6,388,120 B1

CONTINUOUS PROCESS FOR THE MANUFACTURE OF PHOSPHORIC ACID ESTERS

This application is a C-I-P of Ser. No. 09/023,634 filed Feb. 13, 1998, Pat. No. 6,031,035 and claims benefit of Prov. No. 60/083,414 filed Apr. 29, 1998.

FIELD OF THE INVENTION

The present invention relates generally to phosphoric acid esters, and more particularly to a continuous process for producing monomeric bisaryl diphosphates.

BACKGROUND OF THE INVENTION

Bisaryl diphosphates, such as bisphenol A bis(diphenyl)-phosphate are known to be effective flame retardants for polymer resins. For example, a variety of polyphenylene oxide/high-impact polystyrene ("PPO/HIPS") and polycarbonate/acrylonitrile-butadiene-styrene ("PC/ABS") blends all can be improved with bisaryl diphosphate flame retardants.

When using bisaryl diphosphates to impart flame retardancy to plastics it is desired to use compounds having a high percentage of the monomer. This is because monomeric bisaryl diphosphates impart beneficial physical properties to the polymer, which properties are not provided by their dimeric or polymeric counterparts. For example, resins to which monomeric bisaryl diphosphates have been added exhibit improved impact strength, melt flow index, tensile properties and flexural properties when compared to resins combined with dimeric or polymeric aryl phosphates.

Because of their commercial utility, various processes for the manufacture of monomeric bisaryl diphosphates have been developed. For example, it is known that bisphenol A bis(diphenyl)-phosphate can be obtained by catalytically reacting a phosphorus oxyhalide with bisphenol A (BPA) and then reacting the intermediate with phenol.

Prior art processes for making bisphenol A bis(diphenyl) phosphate have been batch processes; neither the reaction of the phosphorus oxyhalide with bisphenol A, nor the reaction of the intermediate with phenol, has been done continuously. However, while batch processes can be adjusted to produce a large amount of monomeric bisaryl diphosphate product, the productivity of such reactions is generally not satisfactory.

Continuous processes may be employed to obtain higher productivity for certain synthetic pathways compared to batch processes. However, application of a continuous process in the formation of phosphoric acid esters would be expected to produce small amounts of monomeric product compared to dimeric, other oligomeric, or polymeric product. Accordingly, the available synthetic pathways suffer from inefficiencies that make them unsuitable for large scale commercial application.

In view of the above, it can be seen that a need exists for improved methods of making phosphoric acid esters such as bisphenol A bis(diphenyl) phosphate. The present invention addresses that need.

SUMMARY OF THE INVENTION

Briefly describing one aspect of the present invention, there is provided a method of making phosphoric acid esters. The method preferably comprises:

(1) continuously reacting a phosphorus oxyhalide with a polyol to produce at least about 60% normalized monomeric halophosphate intermediate; and (2) reacting the monomeric halophosphate intermediate with an alcohol to produce a desired phosphoric acid ester.

In some preferred embodiments, the polyol in Step 1 is a dihydric alcohol and the alcohol in Step 2 is a monohydric alcohol. Conversely, in some preferred embodiments the phosphorus oxyhalide is reacted with a monohydric alcohol to produce at least about 60% normalized monohalomonophosphate diester intermediate. In some embodiments, both the Step 1 and Step 2 reactions are carried out continuously.

One object of the present invention is to provide a method for continuously producing phosphoric acid esters.

Another object of the present invention is to provide a method for producing phosphoric acid esters in a continuous reaction wherein the normalized monomeric halophosphate intermediate content of a reaction between phosphorus oxyhalide and a polyol is at least about 60%, preferably at least about 70%, more preferably at least about 80% and most preferably at least about 90%.

Another object of the present invention is to provide a method for producing phosphoric acid esters in a continuous reaction wherein the normalized monohalomonophosphate diester content of a reaction between phosphorus oxyhalide and a monohydric alcohol is at least about 60%, preferably at least about 70%, more preferably at least about 80% and most preferably at least about 90%.

A further object of the invention is to provide a method for producing monomeric phosphoric acid ester products which can be used as flame retardants, for example, in plastics.

Further objects and advantages of the present invention will be apparent from the following description.

DETAILED DESCRIPTION OF THE PREFERRED EMBODIMENT

Figure 1:
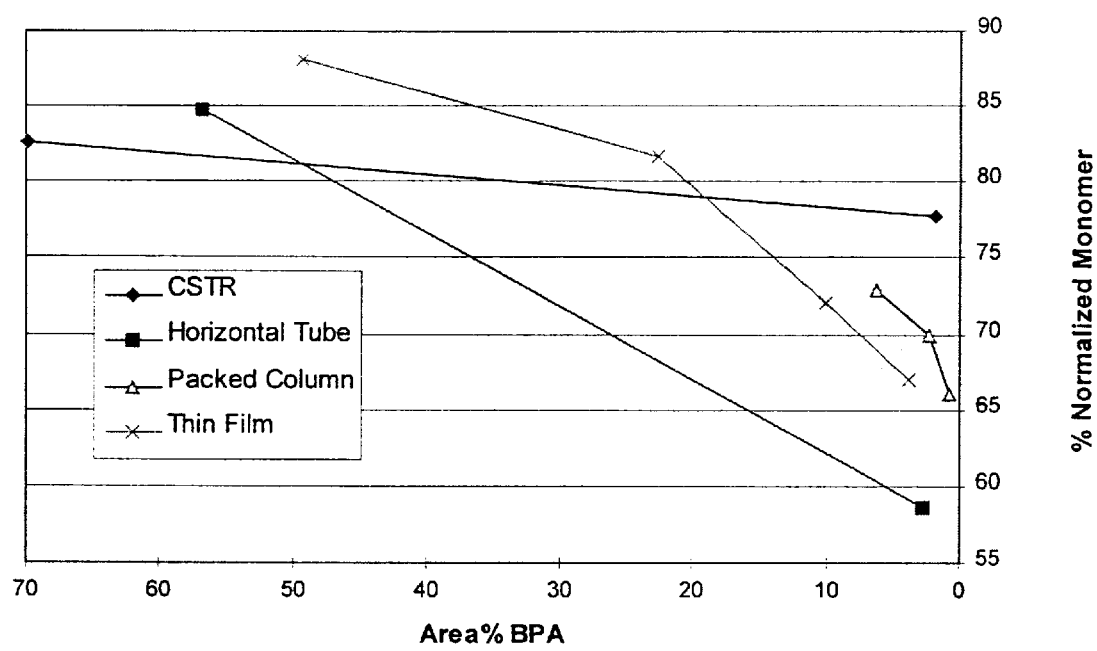
FIG. 1 depicts a graph showing % normalized monomer as a function of area % BPA as a Step 1, Stage 2 reaction is completed for various continuous reactor designs. The reactions were carried out as described in Example 16.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated methods, and such further applications of the principles of the invention as illustrated therein, being contemplated as would normally occur to one skilled in the art to which the invention relates.

As indicated above, the present invention relates generally to a continuous process for producing phosphoric acid esters. It has unexpectedly been discovered that a high monomeric halophosphate intermediate content product can be produced relative to dimeric halophosphate intermediate, along with a high degree of productivity, when the reaction is carried out in a continuous reactor system, such as a continuous stirred tank reactor (CSTR). The intermediate can be used, in certain embodiments, to form a desired monomeric phosphoric acid ester, including BPA bis (diphenyl)-phosphate.

The preferred reactor design (i.e., a continuous reactor) allows the production of product ratios otherwise unattainable in commercial quantities at high productivity. The preferred reactor design is surprising in view of the known role that reactor design plays in determining the degree of oligomerization or polymerization. That is, continuous reactors are less selective than batch processes in reactions where an intermediate or product can react with a raw material or intermediate to form a dimeric product. For example, it would be expected that larger quantities of oligomeric or polymeric products relative to monomeric products would be produced when reactions that form phosphoric acid esters are carried out in a continuous reactor compared to a batch reactor.

The degree of oligomerization or polymerization can further be controlled to some extent by the degree of reaction completion in individual stages of a multiple stage continuous reactor series.

In one aspect of the invention, phosphoric acid esters are continuously produced by a two step process. In the first step, at least about 60% normalized monomeric halophosphate intermediate, preferably a bis(dichlorophosphate), is formed by continuously reacting a phosphorus oxyhalide with an alcohol, preferably a diol or other polyol. After preferably removing the excess phosphorus oxyhalide, the monomeric halophosphate intermediate is reacted with another alcohol, preferably a monohydric alcohol such as a phenol, to produce a desired phosphoric acid ester.

The products of the Step 1 reaction are predominantly monomeric, and, as the monomeric product is used as a reactant in Step 2, the product of the Step 2 reaction will be predominantly monomeric. However, it is recognized that, should one desire an oligomeric or polymeric component after forming the monomeric product from Step 1, the Step 1 monomeric product may be reacted with a polyol in Step 2 and the resultant product may be further processed as desired.

In yet another aspect of the invention, desired phosphoric acid esters are produced by continuously reacting phosphorous oxyhalide with a monohydric alcohol to produce at least about 60% normalized monohalomonophosphate diester intermediate. The intermediate is then reacted with a polyol, preferably a dihydric alcohol, to produce the desired phosphoric acid ester.

Further describing one embodiment of the processes of the present invention, Step 1 of a method for making phosphoric acid esters preferably includes continuously reacting an appropriate alcohol with phosphorus oxyhalide in the presence of a Lewis acid catalyst. The phosphorus oxyhalide used in the present invention is generally of the formula $POX_n$ where X is a halide, including chloride or bromide, and n is preferably 3. Phosphorus oxychloride, $POCl_3$, is the most preferred phosphorus oxyhalide.

Step 1 produces a monomeric halophosphate intermediate when a polyhydric alcohol, such as a dihydric alcohol, is used. In that embodiment, the Step 1 reaction proceeds, diagrammatically, as follows:

Unreacted $POX_3$ is removed by distilling under reduced pressure, leaving the Step 1 intermediate product I. In the above diagram, R is the carbon chain portion (i.e., the aromatic, aliphatic, alicyclic, or combination thereof, portion) of the alcohol, X is a halide as previously mentioned and compound I is the monomeric halophosphate intermediate product of Step 1.

Examples of appropriate alcohols include polyols, such as polyphenols, and including dihydric alcohols such as biphenols, bisphenol A, tetrabromobisphenol A, bisphenol S, bisphenol F, ethylene glycol, 1,4-butane diol, 1,2-hexane diol, resorcinol, catechol, hydroquinone and trihydric alcohols such as glycerine as well as other polyols. The aromatic and alicyclic portions of the alcohols may be alkyl- or halogen-substituted. The aliphatic portion of the alcohol may also be halogen-substituted. The alkyl substituent includes saturated or unsaturated aliphatic hydrocarbon groups which may be either straight chain or branched having a carbon chain length of from 1 to 18. For example, the alkyl group includes methyl, ethyl and structural isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl. The halogen substituent is preferably chlorine and/or bromine. It is further preferred that there is no more than one substituent ortho to each hydroxyl group on an aromatic alcohol.

The catalyst may be any Lewis acid capable of promoting the reaction. Examples include, but are not limited to, $AlCl_3$, $ZnCl_2$, $CaCl_2$, or $MgCl_2$. The catalyst is used in an amount sufficient to allow the reaction to proceed smoothly, and need not be removed from the final product. The amount of catalyst used in Step 1 is typically in the range of about 100 ppm to about 5000 ppm (relative to the other reagents added to the first reactor), preferably 100 ppm to about 1000 ppm and most preferably about 300 ppm to about 700 ppm.

The reaction temperature in Step 1 will be dependent on the specific polyol reacted, but generally an be controlled over a wide range, from about 50° C. to bout 250° C., and the process may be operated at atmospheric pressure, under vacuum, or at an elevated pressure. However, a temperature of about 50° C. to about 200° C. is preferred, a temperature of about 90° C. to about 140° C. is more preferred, and a temperature of about 100° C. to about 110° C. in the first stage and about 110° C. to about 125° C. is most preferred in subsequent stages.

It is to be appreciated that in the first step, the process may be operated with a sufficient excess of $POX_3$ to yield a workable reaction mass at the reaction temperature, or a non-reactive solvent may be used. The phosphorous oxyhalide:polyol mole ratio is typically about 2.5:1 to about 10:1, preferably about 3:1 to about 6:1 and most preferably about 4:1 to about 5:1. The residence time in each reactor may vary from 0.25 hours to about 6 hours.

As briefly mentioned above, the degree of oligomerization or polymerization can further be controlled to some extent by the degree of reaction completion in individual stages of a multiple stage continuous reactor series. The extent of reaction completion in Stage 1 of Step 1 is typically about 10 to about 100%, and about 20% to about 100% in subsequent stages. However, it is preferred that the extent of reaction completion in Stage 1 be about 30% to about 80% and subsequent stages to be about 50% to about 100%. It is most preferred that the extent of reaction completion in Stage 1 be about 30% to about 50%, in Stage 2 about 70% to about 100% and about 85% to about 100% in subsequent stages.

The Step 1 reaction is carried out by continuously reacting the above-described reagents. As described herein, the term "continuously reacting" means that a particular step, such as Step 1 or 2, can be carried out at least partly continuously (i.e., the step can be divided into various stages and at least one stage is carried out continuously) or all of the step can be carried out continuously. The number of stages may range from about 1 to about 5, preferably about 1 to about 3 and most preferably about 2 to about 3.

The term "continuous reactor" as used here refers to a vessel where raw materials or a feed stream containing unreacted or partially reacted material is added continuously or essentially continuously while material is being removed from the vessel to maintain essentially constant reactor volume, and where conditions in the vessel are such that a finite degree of reaction occurs.

As indicated above, the selection of reactor design to accomplish the continuous portion of the reaction in either Step 1 or Step 2 plays an important role in determining the degree of oligomerization or polymerization and the quality of the product. Examples of commercially available reactors that might be used to practice the invention, and that one skilled in the art are familiar with, include falling film or thin film reactors, continuously stirred tank reactors ("CSTR"s), tube reactors, and packed column reactors. Although a wide variety of reactors may be used to practice the invention, CSTRs are preferred.

A series of continuous reactors may employ the same type, or a different type, of reactor. It is further preferred that a CSTR may be used in Stage 1 of a step and then either another CSTR may be used or a batch reactor may be used. It is most preferred to use a series of CSTRs or, alternately, a series of CSTRs with the final stage carried out in a batch reactor.

It is noted that, along with the monomeric product produced in the Step 1 reaction diagramed above, the potential exists for forming dimeric, other oligomeric or polymeric products. For example, referring to the diagram of the Step 1 reaction above, compound I may react with Step 1 reactants (i.e., with the dihydric alcohol and POX$_3$) to form the following dimeric component:

The above dimeric component may also be produced by reaction of the following reactants and intermediates from the Step 1 reaction:

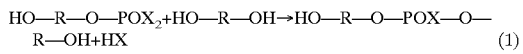 (1)

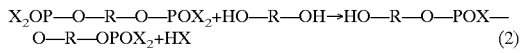 (2)

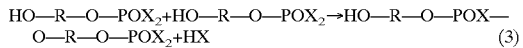 (3)

It is understood that the product formed from (1)–(3) above must be further reacted with POX$_3$ to form the dimeric component.

A convenient measure of the relative amounts of monomer and dimer is the calculation of "normalized monomer" content. Samples are analyzed by liquid chromatography with an ultraviolet detector set at 219 nm. From the resulting chromatogram, the area % monomer and dimer composition is determined. Percent normalized monomer is calculated as % normalized monomer=(area % monomer)/(area % monomer+ dimer)×100%

Stated alternately, the % normalized monomer content represents the percentage of monomer in a product of a specified reaction, such as Step 1 or Step 2, relative to dimer.

The Step 1 reaction preferably forms at least about 60% normalized monomeric halophosphate intermediate. It is further preferred that the Step 1 reaction forms at least about 70%, more preferably at least about 80% and most preferably at least about 90% normalized monomeric halophosphate intermediate.

Referring now to Step 2 of the process, the product of Step 1 is reacted with an alcohol, such as a monohydric alcohol including phenol, similarly under Lewis acid catalysis. In one embodiment, Step 2 may be diagramed as follows:

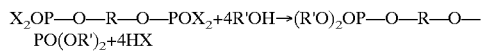

X and R are as defined above for Step 1 and X$_2$OP—O—R—O—POX$_2$ is a monomeric halophosphate intermediate. R'OH is the monohydric alcohol, R' being the carbon chain portion (i.e., the aromatic, aliphatic, alicyclic, or combination thereof, portion) of the alcohol, and (R'O)$_2$OP—O—R—O—PO(OR')$_2$ is the desired phosphoric acid ester product. When R'OH includes an aromatic or alicyclic ring, the aromatic or alicyclic ring may be alkyl or halogen substituted as discussed above for the dihydric alcohol in Step 1. The aliphatic portion of the alcohol may also be halogen-substituted as discussed above. It is further preferred that there is no more than one substituent ortho to each hydroxyl group on an aromatic alcohol. Examples of the alcohol that may be reacted in Step 2 include, but are not limited to, phenol, xylenols, tribromophenol, methanol, t-butanol, cyclohexanol and phenolformaldehyde condensates. It is preferred to carry out Step 2 by reacting the halophosphate intermediate product of Step 1 with phenol using magnesium chloride as a catalyst.

As in the first step, the phenol (or other alcohol) and the Step 1 product can be continuously added in Step 2 to a CSTR. Alternatively, the phenol (or other alcohol) can be added as a single charge to ambient Step 1 product and the resulting mixture added continuously to the reactor.

The discharge from the first continuous reactor may be fed to a second continuous reactor where the material is held at 125–250° C. for a residence time of about 0.25–6 hours. The total phenol charge may be added to the first reactor or split such that part of the total phenol charge is added to the first reactor and the remainder added to the second reactor.

The discharge from the second reactor is fed to an age tank. The age tank is used to feed a continuous or batch vacuum stripper to remove excess alcohol from Step 2, such as phenol. A catalyst is used as in the Step 1 reaction.

The Step 2 reaction is typically performed at a temperature sufficient to convert the halophosphate intermediate to the desired phosphoric acid ester product. Although this temperature may vary depending on the reagents used and the desired product, the temperature of the material in the reactor advantageously ranges from 50° C. to about 250° C., but preferably about 125° C. to about 250° C. The volume of the reactor preferably is adjusted so that the residence time ranges of about 0.25–6 hours.

The mole ratio of alcohol:monomeric halophosphate intermediate is typically about 4:1 to about 5:1, but preferably about 4.04:1 to about 4.40:1, and most preferably about 4.04:1 to about 4.12:1. As in the first step, an excess of the alcohol may be used to improve the ease of processing, or a non-reactive solvent may be employed.

In one preferred embodiment of the first aspect of the invention, BPA is continuously added to magnesium chloride and phosphorus oxychloride in a first CSTR at a temperature of about 100° C. The relative feed rates are such that the mole ratio of phosphorous oxychloride to BPA is about 4:1. The volume of the reactor is maintained to give a residence time of about 1 hour.

The contents of the first reactor are continuously removed and transferred to a second CSTR. In this second reactor the mixture is held at reflux temperature, about 120° C. The feed rates of the input and discharge from the reactor are such that the residence time is about 1 hour.

The discharge from the second reactor is fed to an age tank, which is maintained at about 120° C. while being filled. When this age tank is filled, the discharge from the second reactor is switched to another reactor operating in parallel with the first age tank. The filled age tank is used to feed a distillation to remove the excess $POCl_3$ from the Step 1 product.

The product of Step 1 is then reacted with phenol using magnesium chloride as a catalyst.

As briefly mentioned above, it is to be appreciated that the inventive continuous process may be operated such that part of the first step or second step is performed in a continuous reactor with the rest of the reaction being completed in a batchwise reactor or reactors. Similarly, all of one step may be performed in a continuous reactor or series of continuous reactors, while the other step is done in batch reactors. The steps may be carried out in such a fashion as to maximize production of monomeric halophosphate intermediate product and, consequently, monomeric phosphoric acid ester product.

The productivity of the Step 1 reaction is about 0.05 g to about 2 g monomeric halophosphate intermediate/ml reactor volume/hour. The productivity of Step 1 is more preferably about 0.1 g to about 1 g and most preferably about 0.2 g to about 0.8 g monomeric halophosphate intermediate/ml reactor volume/hour.

The monomer content of the Step 2 reaction product is dependent on the presence of a high percent normalized monomeric halophosphate intermediate which acts as a reactant in Step 2. Thus, if a large amount of monomeric halophosphate intermediate is produced in Step 1 compared to dimeric component, the monomer content of the Step 2 reaction will also be relatively large. That is, relatively large amounts of the monomeric phosphoric acid ester product of Step 2 will be formed compared to dimeric, oligomeric or polymeric phosphoric acid ester product.

Parameters that can affect the properties and quality of the products of Step 1 and Step 2 include catalyst selection and use level, and ratio of phosphorus oxyhalide to alcohol. Each of these parameters has an optimum range to give a flame retardant material with the desired properties. In addition, the moisture content of each starting material has an effect on the final product quality. For example, if the moisture content of the reactants is controlled, a larger amount of monomeric product may be obtained. The effect of moisture on the nature of the product produced is fully described in U.S. Patent No. 6,031,035 and is hereby incorporated by reference in its entirety.

In the case of performing Step 1 or Step 2 in a series of reactors, at least one of which is a continuous reactor, raw materials such as solvent, catalyst, phosphorus oxyhalide, alcohol (i.e., phenol or polyol, such as a diol) may be added to just the first reactor in the series or to downstream reactors in addition to the first. This can be done to improve the ease of processing, to control product quality and/or to obtain the desired product or mixture of products.

In an alternate embodiment, a method of producing phosphoric acid esters is provided that includes continuously reacting phosphorus oxychloride with a chosen monohydric alcohol as described above, such as a phenol, to form a monohalomonophosphate diester intermediate. In this second aspect of the invention, the products from this step are then reacted with the chosen alcohol selected from the alcohols described above, preferably a polyol, such as a diol, to give the desired phosphoric acid ester. This route also utilizes Lewis acid catalysis and continuous addition of reactants as described for the other embodiments. Step 2 product composition and properties are similar to those obtained in the previously described route. It is to be appreciated here that the inventive continuous process may be operated in a similar fashion as described above.

For example, in certain embodiments the reaction of the intermediate with the polyol may also be performed in a continuous reactor. Alternately, the first reaction may be performed in a batch reactor and the second reaction may be performed continuously.

Referring more specifically to the above alternate embodiment, the Step 1 reaction of the monohydric alcohol with the phosphorus oxyhalide may be diagramed as follows:

$$POX_3 + 2R'OH \rightarrow (R'O)_2POX\ (II) + 2HX$$

R'OH and X are as previously defined and compound II is the monohalomonophosphate diester intermediate.

The specific catalyst and the quantity used is the same as in the previous embodiments discussed.

The reaction temperature in Step 1 of the alternate embodiment can also be controlled over a wide range, from about 50° C. to about 250° C., and the process may similarly be operated under various pressures. However, a temperature of 50° C. to about 200° C. is preferred and a temperature of about 90° C. to about 140° C. is more preferred. Moreover, residence times are typically about 0.25 hours to about 6 hours.

The alcohol:phosphorous oxyhalide mole ratio is advantageously about 1.5:1 to about 3:1, and more preferably about 1.75:1 to about 2.25:1.

Reaction of phosphorus oxyhalide with a monohydric alcohol can produce the following undesired compounds:

$$(R'O)POX_2 \tag{III}$$

$$(R'O)_3PO \tag{IV}$$

Compound III is a dihalomonophosphate monoester intermediate and compound IV is a phosphate triester. Compound IV is undesired as this compound can no longer react with a polyol in Step 2 to produce a desired phosphoric acid ester product. Compound III is undesired because it has the potential of reacting with the reactants and intermediates formed in the Step 2 reaction, and can thus lead to formation of dimeric, oligomeric or polymeric Step 2 products. One skilled in the art is aware of the specific undesired reactions that may proceed and products that may be produced so it is not necessary to describe them here.

One skilled in the art, as mentioned above, is also aware that continuous reactions are less selective in reactions where an intermediate or product can react with a raw material or intermediate to form a dimeric component. One skilled in the art would therefore have expected a large amount of compound III and IV to be formed relative to compound II in a continuous reactor compared to a batch reactor. However, by analogy with the reaction described above wherein large amounts of monomeric halophosphate intermediate are formed upon continuously reacting phosphorus oxyhalide with a polyol, it is expected that larger amounts of desired compound II may be formed relative to compounds III and IV when the reaction is carried out in a continuous reactor.

A convenient measure of the relative amounts of compounds II, III and IV is the calculation of "normalized monohalomonophosphate diester" content. Samples are analyzed by liquid chromatography with an ultraviolet detector. From the resulting chromatogram, the area % and compound II, III and IV composition is determined. Percent normalized monhalomonophosphate diester is calculated as % normalized monhalomonophosphate diester (area % compound II)/(area % compound II+compound III+compound IV)×100%

Stated alternately, the normalized monohalomonophosphate diester content represents the percentage of the diester in the product of Step 1 relative to phosphate triesters and dihalomonophosphate monoesters.

The reaction between phosphorus oxyhalide and the monohydric alcohol will typically produce at least about 60% normalized monohalomonophosphate diester. It is further preferred that at least about 70%, more preferably at least about 80% and most preferably at least about 90% of the monohalomonophosphate diester is produced. Similar productivities as in the route described in the previous embodiments should be expected.

Referring now to Step 2 of this alternate embodiment, Step 2 may be diagramed as follows:

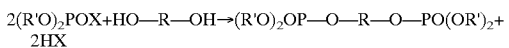

R' and X are as defined above. The Step 2 reaction produces the desired monomeric phosphoric acid ester product, (R'O)$_2$OP—O—R—O—PO(OR')$_2$.

The specific catalyst and the quantity used is the same as in the previous embodiments discussed.

The reaction temperature in Step 2 of the alternate embodiment can also be controlled over a wide range, from about 50° C. to about 250° C., and the process may similarly be operated under various pressures. However, a temperature of about 125° C. to about 250° C. is preferred. Moreover, residence times are typically about 0.25 hours to about 6 hours.

The polyol:monohalomonophosphate diester intermediate mole ratio is advantageously about 0.3:1 to about 0.8:1, and more preferably about 0.4:1 to about 0.6:1. The preferred extents of reaction completion in Step 1 are similar to those described above.

It is to be appreciated that the phosphoric acid esters made by the methods of the present invention, such as bisaryl diphosphates, can be utilized effectively as flame retardants in resin compositions without any further purification. Most preferably, no aqueous washes or distillation steps are used to remove the catalyst from the product. The resin may be a polymer and may include polyphenylene oxide, high-impact polystyrene, polycarbonate, polyurethane, polyvinyl chloride, acrylonitrile-butadiene-styrene, polybutylene terephthalate and mixtures thereof. A wide variety of other polymer resins may also be used. These resins and methods for using phosphoric acid esters as flame retardants are described, for example, in U.S. patent application Ser. No. 09/023,634, filed Feb. 13, 1998.

Reference will now be made to specific examples using the processes described above. It is to be understood that the examples are provided to more completely describe preferred embodiments, and that no limitation to the scope of the invention is intended thereby. For example, it should be evident to one skilled in the art that, although the examples of the invention involve only BPA and POCl$_3$, the invention can be easily applied to any dihydric alcohol and phosphorus oxyhalide.

Furthermore, it is seen in the examples that the monomer content of the desired Step 2 product, the diphosphate ester, is determined by the monomer content of the Step 1 product. Therefore, emphasis has been placed on demonstrating the invention as it applies to Step 1. It will be recognized by one skilled in the art that the invention can also be applied to Step 2.

EXAMPLE 1

Effect of Varying Reaction Conditions on Percent Normalized Monomer Formed Upon Reaction of BPA and POCl$_3$ in a Two-Stage CSTR This example shows that 84.4% normalized monomer is obtained using 4.9 mole POCl$_3$ per mole BPA when Step 1 is performed in a two-stage series of CSTRs, the Stage 1 residence time is 1.5 hours and the Stage 2 residence time is 1 hour.

Stage 1 CSTR

A CSTR was constructed using a glass flask fitted with mechanical stirring, thermocouple, condenser, and heating mantle. BPA was fed continuously to the reactor using a motorized solids addition funnel. MgCl$_2$ catalyst was premixed with the BPA at the desired ratio (more fully described below) prior to charging the BPA to the addition funnel. POCl$_3$ was continuously added to the reactor using a pump. The desired reaction temperature (more fully described below) was maintained using the heating mantle. Concurrent with the addition of BPA, MgCl$_2$, and POCl$_3$, a steady stream of the reaction mixture was removed using a positive displacement pump such that the reaction volume remained constant. A recirculating water scrubber was used to absorb HCl gas vented from the reaction.

Stage 2 CSTR

A second CSTR was constructed using a glass flask fitted with mechanical stirring, thermocouple, condenser and heating mantle. Effluent from the Stage 1 CSTR was fed continuously to the reactor using a positive displacement pump. The desired reaction temperature (more fully described below) was maintained using the heating mantle. Concurrent with the addition of partially reacted material from Stage 1, a steady stream of the Stage 2 reaction mixture was removed using a positive displacement pump such that the reaction volume in Stage 2 remained constant. A recirculating water scrubber was used to absorb HCl gas vented from the reaction.

Start-up 322.7 g POCl$_3$ and 0.30 g MgCl$_2$ were charged to the Stage 1 reactor and heated to 100° C. 139.1 g BPA was added over 1.25 hr while maintaining 100° C. in the reaction mass. No liquid was removed from the reaction during this time.

A constant feed rate of 4.4 ml/min POCl$_3$ was begun and additional mixtures of 138 g BPA and 0.276 g MgCl$_2$ were charged to the addition funnel so the constant feed of the solids was maintained. The instantaneous feed rate of BPA was 2.2 grams per minute, and that of MgCl$_2$ was 0.0044 grams per minute. The mole ratio of POCl$_3$ to BPA (i.e., the molar quantity of POCl$_3$ added to Stage 1 per unit time divided by the molar quantity of BPA added per unit time) was 4.9. Concurrent with the start of the constant POCl$_3$ feed, a constant takeoff was begun to maintain the Stage 1 reaction volume at 610 ml. Temperature was maintained at 102° C. A sample indicated the composition of the reaction mixture at the start of the simultaneous feed and take-off contained 5.3 area % BPA, 68.9 area % monomer, and 14.45 area % dimer. The normalized monomer content was 82.7%.

The Stage 1 reactor was operated with continuous addition of raw materials and removal of reaction mixture for 13.5 hours. Average residence time in the reactor was 1.5 hours. The effluent from Stage 1 stabilized at a composition of 5.8 area % BPA, and 84.8% normalized monomer.

The effluent from Stage 1 was fed to the Stage 2 CSTR which was maintained at reflux under atmospheric pressure and a temperature of 120° C. The volume of the reaction mixture in Stage 2 was controlled at 200 ml by the simultaneous removal of liquid. The average residence time in Stage 2 was 1 hour. The Stage 2 reactor was operated in this way for 6.6 hours. The effluent from Stage 2 stabilized at a composition of <0.1 area % BPA, and 84.4% normalized monomer.

Productivity for the combined Stage 1 and Stage 2 reactors was calculated at 0.14 g monomeric halophosphate intermediate per ml reactor volume per hour during the continuous operation. The concentration of $MgCl_2$ in the Stage 1 feed stream was calculated to be 466 ppm. (grams of $MgCl_2$ per unit time divided by total grams of BPA+ $POCl_3$+$MgCl_2$ per unit time). The low $MgCl_2$ content in the reaction mixture did not, surprisingly, retard the reaction.

EXAMPLE 2

Effect of Varying Reaction Conditions on Percent Normalized Monomer Formed Upon Reaction of BPA and $POCl_3$ in a Two-Stage CSTR This example shows that 77.1% normalized monomer is obtained when Step 1 is performed in a two-stage series of CSTRs, the Stage 1 residence time is 2 hours, the Stage 2 residence time is 3.5 hours and 3.95 mole $POCl_3$ per mole BPA is used.

Similar equipment and procedure as detailed in Example 1 were employed to conduct the Step 1 reaction in a two-stage series of CSTRs. During continuous operation, the first stage reactor was fed at rates of 1.8 g BPA per minute, 0.0036 g $MgCl_2$ per minute, and 2.9 ml $POCl_3$ per minute. The mole ratio of $POCl_3$:BPA was 3.95. Reaction temperature was maintained at 110° C., and the volume of the reaction mass was held at 600 ml. Run time for the continuous reaction was 7.6 hours and the average residence time was 2.0 hr. The effluent stabilized at a composition of 6.24 area % BPA, and 79.4% normalized monomer. The effluent from Stage 1 was fed to Stage 2 to complete the Step 1 reaction.

The Stage 2 reactor was operated at a volume of 500 ml and an average residence time of 3.5 hours. The reaction was held at atmospheric reflux at a temperature of 123° C. The Stage 2 reactor was operated in continuous mode for 8 hours. The effluent stabilized at a composition of 0.36 area % BPA and 77.1% normalized monomer.

Productivity for the combined Stage 1 and Stage 2 reactors was calculated at 0.11 g monomeric halophosphate intermediate per ml reactor volume per hour during the continuous operation. The concentration of $MgCl_2$ in the Stage 1 feed stream was calculated to be 548 ppm.

EXAMPLE 3

Effect of Varying Reaction Conditions on Percent Normalized Monomer Formed Upon Reaction of BPA and $POCl_3$ in a Two Stage CSTR This example shows that 88.5% normalized monomer is obtained when Step 1 is performed in a two-stage series of CSTRs, relatively short residence times are used (i.e., Stage 1 residence time is 0.5 hour and Stage 2 residence time is 1 hour) and the mole ratio of $POCl_3$:BPA is 5.2.

Similar equipment and procedure as detailed in Example 1 were employed to conduct the Step 1 reaction in a two-stage series of CSTRs. During continuous operation, the first stage reactor was fed at rates of 1.8 g BPA per minute, 0.0036 g $MgCl_2$ per minute, and 3.8 ml $POCl_3$ per minute. The mole ratio of $POCl_3$:BPA was 5.2. The reaction temperature was maintained at 88–90° C., and the volume of the reaction mass was held at 175 ml. The run time for the continuous reaction was 22.2 hour and the average residence time was 0.5 hr. The effluent stabilized at a composition of 52.2 area % BPA, and 95.8% normalized monomer. The effluent from Stage 1 was fed to Stage 2 to complete the Step 1 reaction.

The Stage 2 reactor was operated at a volume of 200 ml, and an average residence time of 1 hour. The reaction was held at atmospheric reflux at a temperature of 118° C. The Stage 2 reactor was operated in continuous mode for 7 hours. The effluent stabilized at a composition of 0.8 area % BPA and 88.5% normalized monomer.

Productivity for the combined Stage 1 and Stage 2 reactors was calculated at 0.45 g monomeric halophosphate intermediate per ml reactor volume per hour during the continuous operation. The concentration of $MgCl_2$ in the Stage 1 feed stream was calculated to be 447 ppm. Although the $MgCl_2$ content in the reaction mixture was low, it did not, surprisingly, retard the reaction.

This example further illustrates the ability to adjust the reaction conditions in the two-stage CSTR to extremes. That is, the reaction proceeded for only 0.5 hour at 89° C. in the first stage and only 1 hour at 118° C. in the second stage. The Stage 1 effluent was very high in unreacted BPA. Very high monomer content was obtained (i.e, nearly 90% monomer, with an average n=1.1). Adjustment of reaction conditions allowed control of the monomer content of product. The results of this example may be compared to Example 4 wherein a similar $POCl_3$:BPA mole ratio was used, but the extent of reaction was different in Stage 1.

EXAMPLE 4

Effect of Varying Reaction Conditions on Percent Normalized Monomer Formed Upon Reaction of BPA and $POCl_3$ in a Two-Stage CSTR This example shows that 81.0% normalized monomer may be obtained using 4.9 mole $POCl_3$ per mole BPA when Step 1 is performed in a two-stage series of CSTRs, the Stage 1 residence time is 0.75 hour and the Stage 2 residence time is 2.6 hours. A lower amount of unreacted BPA in Stage 1 (compared to Example 3) resulted in lower monomer in product. The ability to adjust residence time allows finetuning of product quality to desired values.

Similar equipment and procedure as detailed in Example 1 were employed to conduct the Step 1 reaction in a two-stage series of CSTRs. During continuous operation, the first stage reactor was fed at rates of 1.8 g BPA per minute, 0.0036 g $MgCl_2$ per minute, and 3.6 ml $POCl_3$ per minute. The mole ratio of $POCl_3$:BPA was 4.9. The reaction temperature was maintained at 110° C., and the volume of the reaction mass was held at about 300 ml. The run time for the continuous reaction was 7.5 hours and the average residence time was 0.75 hr. The effluent stabilized at a composition of 7.2 area % BPA, and 81.9% normalized monomer. The effluent from Stage 1 was fed to Stage 2 to complete the Step 1 reaction.

The Stage 2 reactor was operated at a volume of 350 ml, and an average residence time of 2.6 hours. The reaction was held at atmospheric reflux at a temperature of 120° C. The Stage 2 reactor was operated in continuous mode for 7.5 hours. The effluent stabilized at a composition of 0.6 area % BPA and 81.0% normalized monomer.

Productivity for the combined Stage 1 and Stage 2 reactors was calculated at 0.18 g monomeric halophosphate intermediate per ml reactor volume per hour during the continuous operation. The concentration of $MgCl_2$ in the Stage 1 feed stream was calculated to be 466 ppm.

EXAMPLE 5

Use of a Combination of a Batch Reactor and a CSTR in Step 1

This example illustrates the ability to employ a combination of continuous and batch reactors to effect the formation of the bis-chlorophosphate ester, which can then be used in Step 2. This example specifically shows that 83.8% normalized monomer is obtained using 5.0 mole $POCl_3$ per mole BPA when Stage 1 of Step 1 is performed in a CSTR, Stage 2 is performed in a batch reactor, the Stage 1 residence time is 0.6 hour and the Stage 2 residence time is about 1 hour.

A series of Step 1 reactions were performed in which a CSTR was used for the first stage of the reaction of BPA with $POCl_3$. The partially reacted mixture was collected and the reaction was completed in a batch reactor. Specifically, the Stage 1 effluent was collected in a receiver and about every hour the receiver was replaced. The filled receiver was heated to reflux and the reflux was maintained for a period of time such that the reaction was essentially completed.

The Stage 1 CSTR was operated at 110° C. with a volume of 220 ml and average residence time of 0.6 hr. Continuous feed rates were 1.8 g/min BPA, 0.0036 g/min $MgCl_2$, and 3.7 ml/min $POCl_3$. The mole ratio of $POCl_3$:BPA was 5.0. A receiver, analyzed to contain 12.4 area % BPA and 85.8% normalized monomer, was fitted with a magnetic stir bar, heating mantle and condenser. The receiver contents were quickly heated to reflux, which was maintained for 0.75 hours. The reaction product contained 1.0 area % BPA and 81.5% normalized monomer.

A later receiver from the same Stage 1 CSTR was produced under conditions of 110° C., 0.6 hr residence time, 220 ml reactor volume and a $POCl_3$:BPA mole ratio of 5.4. Stage 1 effluent contained 9.1 area % BPA and 85.3% normalized monomer. After refluxing the receiver contents for 1.25 hours the reaction mixture contained <0.1 area % BPA and 83.8% normalized monomer.

EXAMPLE 6

Use of a Combination of Batch reactor and a CSTR When the CSTR Step 1, Stage 1 Reactor is Operated at Reflux This example illustrates the percent normalized monomer formed when operating the Stage 1 CSTR reactor at reflux and using a Stage 2 batch reactor.

The procedure in Example 5 was followed, with the exception that a Stage 1 CSTR was operated at atmospheric reflux at a temperature of 113° C., and the $POCl_3$:BPA mole ratio was 5.1. A receiver containing 6.9 area % BPA and 84.2% normalized monomer was refluxed as a batch reaction for 0.6 hours to essentially complete the reaction. The product contained 0.2 area % BPA and 81.7% normalized monomer.

EXAMPLE 7

Effect of Amount of Catalyst on % Normalized Monomer

This example illustrates a higher % normalized monomer (than in comparable reaction of Example 5) is obtained when Stage 1 of Step 1 is performed in a CSTR with twice the normal catalyst quantity and Stage 2 is performed in a batch reactor.

Following the procedure in Example 5, a Stage 1 CSTR was operated at 110° C. The continuous feed rates were 1.8 g/min BPA, 0.0072 g/min $MgCl_2$ and 3.7 ml/min $POCl_3$. The average residence time was 0.6 hours. A receiver containing 18.2 area % BPA and 88.9% normalized monomer was refluxed for 1.25 hours in a batch reaction. The product contained <0.1 area % BPA and 84.9% normalized monomer.

EXAMPLE 8

Use of a Combination of a CSTR and a Horizontal Tube Reactor (HTR) in Step 1

This example illustrates the variety of continuous reactors designs that are possible by carrying out Stage 1 of Step 1 with a CSTR and Stage 2 with an HTR.

A 12-inch long by 4 inch inner diameter jacketed glass pipe was supported horizontally. Hot oil between 130° C. and 150° C. was circulated through the jacket to heat the reaction mixture. Partially reacted BPA, $POCl_3$ and $MgCl_2$ exiting the Stage 1 CSTR was collected and fed to the tube reactor using a positive displacement pump. The tube reactor was operated only partially full to allow disengagement of the HCl gas produced. The exit temperature of the reaction was monitored and the effluent was collected in a receiver which was periodically analyzed by liquid chromatography. The vent gas from the reactor was passed through a condenser to prevent loss of $POCl_3$.

The reactor was fed at a constant rate such that the desired average residence time was achieved. The average residence time for Stage 1 was 30 minutes and the average residence time for Stage 2 was 55 minutes. Stage 1 continuous feed rates were 1.9 g/min BPA, 0.0036 g/min $MgCl_2$ and 4.4 ml/min $POCl_3$.

Effluent from a Stage 1 CSTR was collected which contained 58 area % BPA and 88.9% normalized monomer. The $POCl_3$:BPA mole ratio in Stage 1 was 5.3. The Stage 1 effluent was fed to the Stage 2 tube reactor at a rate of 0.64 ml per minute. The oil temperature was maintained at 150° C. and the effluent temperature was 131° C. The Stage 2 reactor was operated continuously for 7 hours. The effluent stabilized at a composition of 0.5 area % BPA and 58.1% normalized monomer.

EXAMPLE 9

Effect of Residence Time on % Normalized Monomer When Stage 1 is Performed in a CSTR and Stage 2 is Performed in an HTR This example shows that 69.9% monomer is obtained using a continuous reactor for Stage 1, an HTR for Stage 2, and a $POCl_3$:BPA mole ratio of 4.4.

The HTR as described in Example 8 was used to further react effluent from a Stage 1 CSTR. Continuous feed rates for the Stage 1 CSTR were 2.2 g/min BPA, 0.0044 g/min $MgCl_2$ and 3.8 ml/min $POCl_3$ and the average residence time in the Stage 1 reactor was 2 hours. The mole ratio of POCl$_3$:BPA in the first stage was 4.4, and the material fed to the Stage 2 tube reactor was analyzed to contain 56.9 area % BPA and 84.8% normalized monomer. The tube reactor was operated with an average residence time of 29 minutes, hot oil temperature of 130° C. and effluent temperature of 114° C. The Stage 2 effluent contained 16.1 area % BPA and 69.9% normalized monomer. This partially completed mixture was suitable for reaction completion in subsequent stages.

EXAMPLE 10

Use of a Combination of a Thin Film Reactor and a CSTR in Step 1

This example illustrates the % normalized monomer obtained when Stage 1 of Step 1 is performed in a CSTR and Stage 2 is performed in a thin film reactor.

The Stage 1 reaction was performed in a CSTR with continuous feed rates of 2.2 g/min BPA, 0.0044 g/min MgCl$_2$ and 4.1 ml/min POCl$_3$. The average residence time in the Stage 1 reactor was 0.5 hours.

A jacketed column 24 inches in height with 1 inch inner diameter was supported vertically. Oil at a temperature of 150° C. was circulated through the jacket. Partially reacted effluent from the Stage 1 CSTR reaction of BPA, POCl$_3$ and MgCl$_2$ was fed continuously to the top of the reactor where it was distributed evenly to the heated column by a perforated plate. The reaction mixture flowed down the column as a thin film, and was collected in a receiver.

Effluent from the Stage 1 CSTR was collected and contained 49.3 area % BPA and 88.1% normalized monomer. The POCl$_3$:BPA molar ratio in Stage 1 was 4.57. The Stage 1 effluent was fed to the Stage 2 thin film reactor at a rate of 1.4 ml per minute with an average residence time of 4 minutes. The oil temperature was maintained at 150° C. and the effluent temperature was 110° C. The Stage 2 reactor was operated continuously for 9.75 hours. The effluent stabilized at a composition of 22.7 area % BPA and 81.6% normalized monomer.

The effluent from the first pass through the thin film reactor was collected and fed through at the same conditions of temperature and residence time for a second and third time. Results are summarized in Table 1.

TABLE 1

Area % BPA and % Normalized Monomer.

| Thin Film reactor pass | Effluent Area % BPA | Effluent Normalized monomer |
|---|---|---|
| Stage 1 | 49.3% | 88.1% |
| 1 | 22.7% | 81.6% |
| 2 | 10.1% | 72.1% |
| 3 | 3.8% | 67.0% |

EXAMPLE 11

Use of a Combination of a Packed Column Reactor and a CSTR in Step 1

This example illustrates the % normalized monomer obtained when Stage 1 and Stage 2 are performed in a CSTR and stage 3 is performed in a packed column reactor.

The Stage 1 reaction was performed in a CSTR with continuous feed rates of 2.3 g/min BPA, 0.0044 g/min MgCl$_2$ and 4 ml/min POCl$_3$. The average residence time in the Stage 1 reactor was 3.8 hours. The POCl$_3$:BPA molar ratio in Stage 1 was 4.4. The reaction temperature in the Stage 1 reactor was 90° C. The effluent from Stage 1 was fed at 4 ml/min to a second CSTR operating at 117° C. with a residence time of 2 hours.

A jacketed column 24 inches in height with 1 inch inner diameter was supported vertically and packed with ⅝ inch ceramic saddles. 150° C. oil was circulated through the jacket. Partially reacted effluent from the Stage 1 CSTR reaction of BPA, POCl$_3$ and MgCl$_2$ was fed continuously to the top of the reactor where it was distributed evenly to the packed column. The reaction mixture flowed down through the column, and was collected in a receiver.

Effluent from a Stage 2 CSTR was collected which contained 6.3 area % BPA and 72.9% normalized monomer. The Stage 2 effluent was fed to the Stage 3 packed column reactor at a rate of 1.3 ml per minute. Average residence time was 4 minutes. The oil temperature was maintained at 150° C. and the effluent temperature was 91° C. The Stage 2 reactor was operated continuously for 11 hours. The effluent stabilized at a composition of 2.3 area % BPA and 69.9% normalized monomer.

The effluent from the first pass through the packed column reactor was collected and fed through at the same conditions of temperature and residence time for a second time. The effluent contained 0.8 area % BPA and 66.1% normalized monomer.

EXAMPLE 12

Use of CSTR in a Multi-Stage Step 1 and a Batch Reactor in Step 2

This example shows the % normalized monomer formed when Stages 1 and 2 of Step 1 are performed in a CSTR and Step 2 is performed in a batch reactor.

945 grams of Step 1 product made in Example 1 was charged to a stirred flask fitted with a heating mantle, temperature controller and vacuum distillation head with condenser. The flask was slowly heated to 180° C. while reducing the pressure to 20 torr to remove remaining POCl$_3$. Vacuum was relieved with nitrogen and the flask was allowed to cool. The stripped Step 1 product was analyzed to contain 84.0% normalized monomer.

320.3 grams phenol was charged into an addition funnel wrapped with heat tape. The distillation head was replaced with a reflux condenser. Phenol was added over 90 minutes to the flask while maintaining a reaction temperature of 160° C. An hour after the addition was complete, a subsurface nitrogen sparge was introduced into the reactor. The reaction was monitored for completion by liquid chromatography. When the reaction was complete, vacuum was applied to the flask to remove the remaining phenol. The final product was analyzed by liquid chromatography and found to contain 94.5% by area bisaryl diphosphate (monomer and dimer), 82.3% normalized monomer, and 0.67 wt % triphenyl phosphate.

EXAMPLE 13

Effect of Varying Reaction Conditions on Percent Normalized Monomer Formed Upon Reaction of BPA and POCl$_3$ in a Two-Stage CSTR This example shows 80.1% normalized monomer, and relatively high productivity, is obtained when Step 1 is performed in a two-stage series of CSTRs, the Stage 1 residence time is 0.5 hour, the Stage 2 residence time is 1 hour and the mole ratio of $POCl_3$:BPA is 4.2.

Similar equipment and procedure as detailed in Example 1 were employed to conduct the Step 1 reaction in a two-stage series of CSTRs. During continuous operation, the first stage reactor was fed at rates of 1.8 g BPA per minute, 0.0036 g $MgCl_2$ per minute, and 3.1 ml $POCl_3$ per minute. The mole ratio of $POCl_3$:BPA was 4.2. The reaction temperature was maintained at 93° C., and the volume of the reaction mass was held at 150 ml. The run time for the continuous reaction was 13 hours and the average residence time was 0.5 hr. The effluent stabilized at a composition of 39.6 area % BPA, and 91.1% normalized monomer. The effluent from Stage 1 was fed to Stage 2 to complete the Step 1 reaction.

The Stage 2 reactor was operated at a volume of 200 ml, and an average residence time of 1 hours. The reaction was held at atmospheric reflux at a temperature of 123° C. The Stage 2 reactor was operated in continuous mode for 6.35 hours. The effluent stabilized at a composition of 0.35 area % BPA and 80.1% normalized monomer. The concentration of $MgCl_2$ in the Stage 1 feed stream was calculated to be 522 ppm.

Productivity for the combined Stage 1 and Stage 2 reactors was calculated at 0.58 g monomeric halophosphate intermediate per ml reactor volume per hour during the continuous operation.

EXAMPLE 14

Comparative Example: Batch Reaction in Steps 1 and 2

This example shows that, although 81% normalized monomer was obtained in a batch process, the productivity of the reaction was less than can be obtained in some of the preceding Examples utilizing continuous reactors.

Step 1

$POCl_3$ (671.0 g, 4.38 moles) and $MgCl_2$ (0.58 g, 0.0061 moles) were charged into a flask equipped with a stirrer, heating mantle, temperature controller and a reflux condenser vented to a water absorber. The flask contents were heated to 100° C. BPA (288.5 g, 1.26 moles) was placed in a solids addition funnel and added to the flask over the course of 3 hours. At that time, the flask contents were heated to reflux and the reaction monitored for completion by liquid chromatography. Complete reaction required 2 hours reflux. After the reaction was complete, the flask was equipped for distillation and vacuum gradually applied until the pressure was less than 20 torr. The temperature of the flask contents was allowed to increase to 180° C. during this process. When the temperature reached 180° C., the distillation was stopped and the material was subsequently used in the second Step. The Step 1 product was analyzed by liquid chromatography and found to contain 81.4% normalized monomer.

Step 2

The contents of the flask from Step 1 were heated to 165° C. Phenol (432.6 g, 4.60 moles) was charged into an addition funnel wrapped with heat tape. The phenol was added to the reactor over the course of 2 hours. An hour after the addition was complete, a subsurface nitrogen sparge was introduced into the reactor. The reaction was monitored for completion by liquid chromatography. When the reaction was complete, vacuum was applied to the flask to remove the remaining phenol. The final product was analyzed by liquid chromatography and found to contain 98.7% by area bisaryl diphosphate (monomer and dimer), 81.0% normalized monomer, and 0.76 wt % triphenyl phosphate.

Productivity for the Step 1 reactor was calculated at 0.15 g monomeric halophosphate intermediate per hour per ml reactor volume during the operation. The concentration of $MgCl_2$ in the Step 1 feed stream was calculated to be 604 ppm. The productivity was calculated from the time between the start of the BPA feed to the end of the reflux, and does not include the time required to charge and discharge from the reactor, which can be significant. Even if the productivity of the batch reactor were doubled, it would not approach the rates of Examples 3 or 13 (0.45 g/ml/hr and 0.58 g/ml/hr, respectively).

EXAMPLE 15

Comparative Example: Extent of Decrease of % Normalized Monomer Formed in Batch Reactors This example shows that the % normalized monomer decreases sharply as the Step 1 reaction completes. It was seen in Examples 12 and 14 that the monomer content of the Step 1 product determines the monomer content in the Step 2 product. Preferred reaction conditions are those resulting in Step 1 product containing at least about 60% normalized monomer, further preferably at least about 70%, more preferably at least about 80% and most preferably at least about 90% normalized monomer.

A Step 1 reaction was conducted in a batch reactor as described in Example 14. The reaction was sampled periodically throughout the BPA addition and reflux period. Results of the liquid chromatography analyses are shown in Table 2 below.

TABLE 2

Area % BPA and % Normalized Monomer as a Function of Reaction Completion in a Batch Reactor.

| Time (hr.) | Area % BPA | % Normalized monomer | Comments |
|---|---|---|---|
| 0 | | | Begin BPA addition |
| 1 | 10.8 | 96.6 | |
| 2 | 12.4 | 93.4 | |
| 3.33 | 24.8 | 90.9 | BPA addition complete |
| 3.66 | 4.1 | 86.2 | |
| 4 | 0 | 82.4 | |

It is seen in Table 2 that, as the reaction completes, the monomer content relative to the dimer decreases.

EXAMPLE 16

Extent of Decrease of % Normalized Monomer Formed in Various Continuous Reactors A series of continuous Step 1 reactions were conducted using a CSTR for Stage 1, and a variety of continuous reactor types for Stage 2. The reactor types and their operation are described in the preceding examples. The decrease in normalized monomer content as the reaction is completed is illustrated in Table 3 with data from the Stage 2 reactions.

TABLE 3

Area % BPA and % Normalized Monomer as a Function of Reaction Completion in Various Continuous Reactors.

| Stage 2 Reactor type | | Area % BPA | % Normalized Monomer |
|---|---|---|---|
| CSTR | Feed | 69.9 | 82.6 |
| | Effluent | 1.8 | 77.8 |
| Horizontal Tube | Feed | 56.9 | 84.8 |
| | Effluent | 2.7 | 58.7 |
| Packed Column | Feed | 6.3 | 72.9 |
| | First Pass Effluent | 2.3 | 69.9 |
| | Second Pass Effluent | 0.8 | 66.1 |
| Thin Film | Feed | 49.3 | 88.1 |
| | First Pass Effluent | 22.7 | 81.6 |
| | Second Pass Effluent | 10.1 | 72.1 |
| | Third Pass Effluent | 3.8 | 67.0 |

Table 3 data was plotted and is shown in FIG. 1. It can be seen in FIG. 1 that the CSTR allows retention of high monomer levels as the reaction is completed. The linear reactor designs, those where the reaction progress changes as the material moves through the reactor, all show about the same rate of monomer decrease with reaction progress. The packed column curve parallels that for the thin film reactor for feeds below about 10% BPA. The CSTR stands out as having the smallest change in % normalized monomer.

EXAMPLE 17

Comparison of Stage 2 CSTR Performance with Varying POCl$_3$ Ratios

Figure 2:
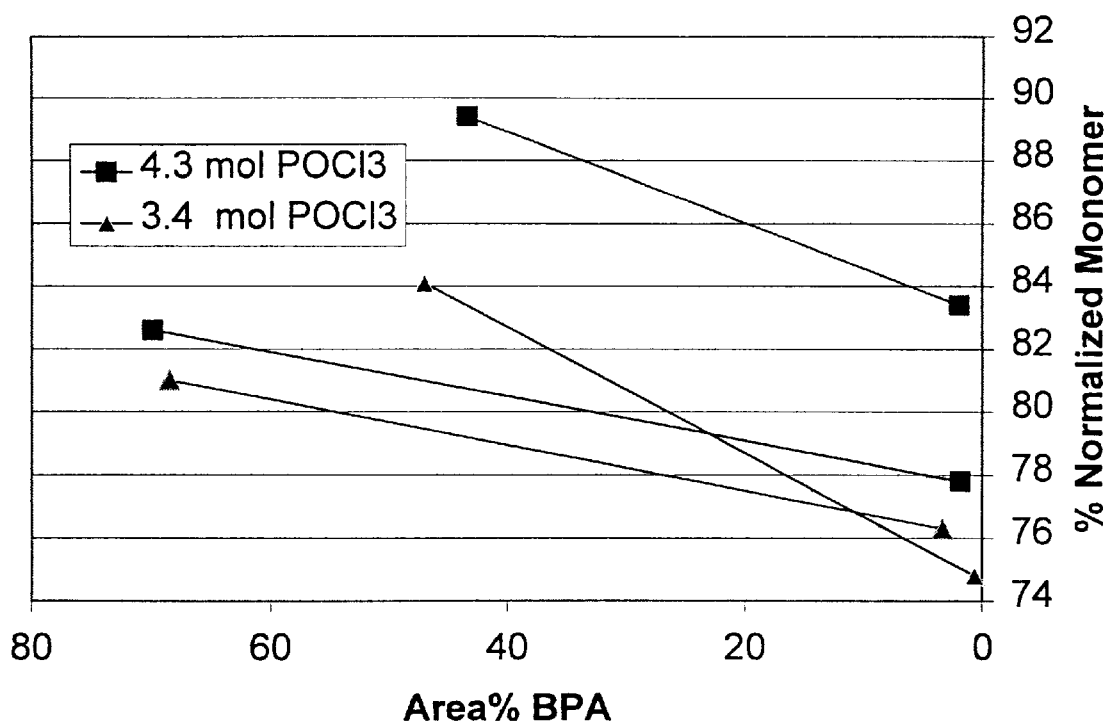
FIG. 2 depicts a graph showing the efficiency of a Step 1, Stage 2 reaction performed in a continuous stirred tank reactor % when the $POCl_3$:BPA molar ratio is varied. The graph specifically depicts % normalized monomer as a function of area % BPA. The reactions were carried out as described in Example 17.

A series of Stage 2 CSTR reactions were conducted as described in the preceding examples. The ratio of POCl$_3$ to BPA was varied, as was the extent of reaction completion in Stage 1. The results of these experiments are found in Table 4 below and are shown graphically in FIG. 2.

TABLE 4

Area % BPA and % Normalized Monomer as a Function of the POCl$_3$:BPA Molar Ratio.

| Stage 2 CSTR Reference | POCl$_3$ to BPA Mole ratio in Stage 1 | Stage 2 | Area % BPA | % Normalized Monomer |
|---|---|---|---|---|
| A | 4.3 | Feed | 69.9 | 82.6 |
| | | Effluent | 1.8 | 77.8 |
| B | 4.3 | Feed | 43.4 | 89.4 |
| | | Effluent | 1.9 | 83.4 |
| C | 3.4 | Feed | 47.0 | 84.1 |
| | | Effluent | 0.6 | 74.8 |
| D | 3.4 | Feed | 68.5 | 81.0 |
| | | Effluent | 3.3 | 76.3 |

A, 30.1% reaction in Stage 1
B, 56.6% reaction in Stage 1
C, 53% reaction in Stage 1
D, 31.5% reaction in Stage 1

Table 4 shows that the normalized monomer content of the Stage 2 CSTR product is influenced by both the POCl$_3$:BPA mole ratio used in Stage 1 and the degree of reaction completion in Stage 1. One can obtain Step 1 products containing between about 80 and 90% normalized monomer content by employing a variety of continuous reaction conditions and reactor types, but operation of a multiple stage CSTR to complete the majority of the reaction is demonstrated as an efficient means of commercial production.

Figure 3:
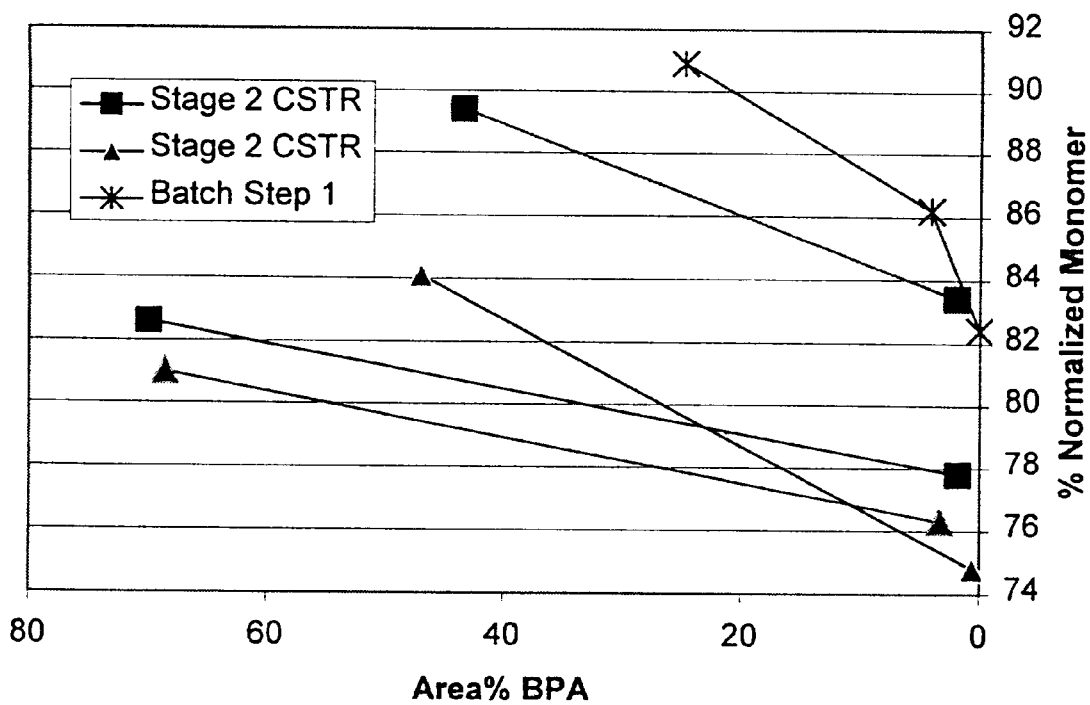
FIG. 3 depicts a graph showing % normalized monomer as a function of area % BPA by performing Step 1, Stage 2 in a continuous stirred tank reactor and a batch reactor when the $POCl_3$:BPA molar ratio is varied. The reactions were carried out as described in Examples 15 and 17.

Furthermore, the Step 1 CSTR reactions were compared to the reaction progress of the batch Step 1 from Example 15. It is seen in FIG. 3 that the profile of the normalized monomer decrease with reaction completion for the CSTR is very similar to that of the batch reaction.

These results are the opposite of what is predicted by the underlying principles of continuous reactions. In reactions where an intermediate or product can react with a raw material or intermediate to form a dimeric product, batch reactions typically give greater amounts of monomer than CSTR's. Within the range of continuous reactor designs, "plug flow" or "linear" reactor designs typically mimic the performance of batch reactors. Examples of this type of continuous reactor are the thin film and horizontal tube reactor. The packed column reactor deviates from plug flow more than these, but is still considered in the same category. The CSTR is expected to produce the lowest normalized monomer content of all continuous reactor designs, since substantial concentrations of product and intermediate are in contact with fresh raw materials with which they can react to form dimeric products.

It can be predicted that reaction of a dihydric alcohol with a phosphorus oxyhalide will result in higher concentrations of monomeric product compared to dimeric product if the phosphorus oxyhalide is present in greater excess. However, it is not expected that a CSTR, the reactor expected to enhance the formation of polymers, would produce high levels of monomer with a small increase in the excess phosphorus oxyhalide compared to the excess used in a batch reaction. Moreover, it is also not expected that by increasing the excess of phosphorus oxyhalide and keeping the catalyst charge constant, thereby reducing the concentration of catalyst relative to the batch reaction, the productivity of the continuous reaction would exceed that of the batch reaction.

While the invention has been illustrated and described in detail in the foregoing description, the same is to be construed as illustrative and not restrictive in character, it being understood that only the preferred embodiment has been shown and described and that all changes and modifications that come within the spirit of the invention are desired to be protected.

What is claimed is:

1. A method of making diphosphoric acid esters of the formula:

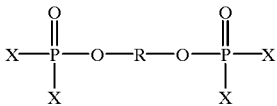

wherein R=is the residue of an aromatic or aliphatic diol; and wherein X=is bromine or chlorine; said method comprising:

continuously reacting a phosphorus oxyhalide with a diol to produce at least about 60% normalized monomeric halophosphate;

wherein said reacting is done as a non-aqueous process in a series of at least two mixed flow reactors, and wherein said reacting is done at a temperature of between about 50° C. to about 200° C.

2. The method of claim 1, wherein the phosphorus oxyhalide:diol mole ratio is about 2.5:1 to about 10:1.

3. The method of claim 2, wherein the phosphorus oxyhalide:diol mole ratio is about 4:1 to about 5:1.

4. The method of claim 1, wherein said continuously reacting a phosphorus oxyhalide with a diol is carried out in the presence of a catalyst.

5. The method of claim 4, wherein said catalyst is a Lewis acid.

6. The method of claim 5, wherein said Lewis acid is a metal halide salt.

7. The method of claim 6, wherein said metal halide salt is selected from the group consisting of aluminum chloride, zinc chloride, calcium chloride and magnesium chloride.

8. The method of claim 1, wherein said phosphorus oxyhalide is phosphorus oxychloride.

9. The method of claim 1, wherein said diol is bisphenol A.

10. The method of claim 1, wherein the productivity of said continuous reaction is about 0.05 g/ml reactor volume/hour to about 2.0 g/ml reactor volume/hour of said diphosphorotetrahalidate.

11. The method of claim 1, wherein said continuously reacting a phosphorus oxyhalide with a diol is performed in a continuous stirred tank reactor.

12. The method of claim 11, wherein the reaction is performed in at least two stages in at least two continuous stirred tank reactors.

13. The method of claim 1 wherein said continuously reacting continuously reacts a phosphorus oxyhalide with a polyol to produce at least about 70% normalized monomeric halophosphate.

14. The method of claim 1 wherein said continuously reacting continuously reacts a phosphorus oxyhalide with a polyol to produce at least about 80% normalized monomeric halophosphate.

15. The method of claim 1 wherein said continuously reacting continuously reacts a phosphorus oxyhalide with a polyol to produce at least about 90% normalized monomeric halophosphate.

* * * * *